US010119940B2

(12) United States Patent
Tat et al.

(10) Patent No.: US 10,119,940 B2
(45) Date of Patent: Nov. 6, 2018

(54) ACOUSTIC EMISSION SENSOR HOLDER

(71) Applicant: The Boeing Company, Chicago, IL (US)

(72) Inventors: Hong H. Tat, Redmond, WA (US); John A. Mittleider, Kent, WA (US); Joseph D. Schaefer, St. Louis, MO (US); Scott H. Gardner, Burien, WA (US); James W. Edwards, Renton, WA (US); Tyler M. Holmes, Seattle, WA (US)

(73) Assignee: The Boeing Company, Chicago, IL (US)

( * ) Notice: Subject to any disclaimer, the term of this patent is extended or adjusted under 35 U.S.C. 154(b) by 57 days.

(21) Appl. No.: 15/246,654

(22) Filed: Aug. 25, 2016

(65) Prior Publication Data

US 2018/0059064 A1 Mar. 1, 2018

(51) Int. Cl.
*G01N 29/22* (2006.01)
*F16M 13/02* (2006.01)
(Continued)

(52) U.S. Cl.
CPC ............ *G01N 29/223* (2013.01); *B23P 19/00* (2013.01); *F16M 13/02* (2013.01); *G01N 29/04* (2013.01);
(Continued)

(58) Field of Classification Search
CPC ...... G01N 29/04; G01N 29/14; G01N 29/223; G01N 2291/0231; G01N 2291/0232;
(Continued)

(56) References Cited

U.S. PATENT DOCUMENTS 3,894,205 A * 7/1975 List .................. H01R 33/46
                                               200/51.07
4,858,470 A   8/1989 Kincaid
(Continued)

FOREIGN PATENT DOCUMENTS

EP      0403807 A2   12/1990

OTHER PUBLICATIONS

European Search Report in corresponding application No. 17178629.6, dated Dec. 13, 2017.
(Continued)

*Primary Examiner* — Tan Le
(74) *Attorney, Agent, or Firm* — Ostrager Chong Flaherty & Broitman PC

(57) ABSTRACT

A holder for attaching an acoustic emission sensor to a non-metallic and non-magnetic material has a tubular body with a closed top end and an open bottom end through which the sensor is insertable into the tubular body. The closed top end has a plurality of unitary flexible flaps angularly extending inwardly from an inner surface of the enclosed top end. An inner surface of the tubular body has a plurality of spacers extending radially inward proximate the bottom end of the tubular body. The unitary flexible flaps and the spacers fix the sensor within the tubular body. The tubular body may also have a plurality of capture tabs extending outwardly from an exterior surface thereof proximate the open bottom end that are slidably and removably engageable with an engagement keyway in a retainer bracket that is affixed to a non-metallic and non-magnetic material.

17 Claims, 8 Drawing Sheets

(51) Int. Cl.
*B23P 19/00* (2006.01)
*G01N 29/04* (2006.01)
*G01N 29/14* (2006.01)
*G10K 11/00* (2006.01)

(52) U.S. Cl.
CPC ........... *G01N 29/14* (2013.01); *G10K 11/004* (2013.01); *G01N 2291/0231* (2013.01); *G01N 2291/0232* (2013.01); *G01N 2291/0258* (2013.01); *G01N 2291/101* (2013.01); *G01N 2291/106* (2013.01); *G01N 2291/2638* (2013.01); *G01N 2291/2694* (2013.01)

(58) Field of Classification Search
CPC ..... G01N 2291/0258; G01N 2291/101; G01N 2291/106; G01N 2291/2638; G01N 2291/2694; G10K 11/004; G01D 11/245; F16M 13/02
USPC ............ 248/27.1, 27.3, 311.2, 314; 439/536, 439/669; 403/140, 141; 362/266; 73/866.5
See application file for complete search history.

(56) References Cited

U.S. PATENT DOCUMENTS

| | | | |
|---|---|---|---|
| 4,905,518 A | | 3/1990 | Kubler |
| 5,094,524 A | * | 3/1992 | Fuhr ..................... A61B 3/024 351/203 |
| 5,542,859 A | * | 8/1996 | Ison ...................... H01R 13/74 248/27.1 |
| 6,134,968 A | | 10/2000 | Kunze, Jr. |
| 6,761,078 B2 | | 7/2004 | Allen |
| 7,412,900 B2 | * | 8/2008 | Santos ................... G01D 11/30 73/855 |
| D747,692 S | * | 1/2016 | Katagiyama ................. D13/154 |
| 2007/0267941 A1 | | 11/2007 | Eidel et al. |
| 2014/0347959 A1 | | 11/2014 | Kirakawa |
| 2016/0038105 A1 | * | 2/2016 | Hayman ................ A61B 6/145 378/153 |
| 2016/0098624 A1 | * | 4/2016 | Chompff ............... G09F 3/0295 235/494 |

OTHER PUBLICATIONS

Soundwel Acoustic Emission Accessories, http://www/soundwel.cn/enproducts/144.html, printed Jul. 27, 2016, Soundwel Technology Ltd., China.
Airtech Advanced Materials Group, Safety Information Sheet, Sealant Tapes, Material No. 1027, Jul. 14, 2015, Airtech International, Inc., Huntington Beach, CA.
Accessories for Acoustic Emission Systems, Specification, Vallen Systeme, Icking, Germany, Feb. 2016.
Magnetic Hold Downs, Physical Acoustics, Princeton Junction, NJ printed from www.physicalacoustics.com/by-product/magnetic-hold-downs on Aug. 24, 2016.

\* cited by examiner

ACOUSTIC EMISSION SENSOR HOLDER

TECHNICAL FIELD

This disclosure generally relates to holders for maintaining the positioning and surface contact of sensors on an article during testing, and more particularly to acoustic emission sensor holders for use during environmental testing of non-metallic and non-magnetic materials, such as composite or ceramic materials.

BACKGROUND

Environmental conditions may affect materials used to make vehicles and other types of structures intended for outdoor use or for use in extreme environments, such as aerospace structures that experience dynamic and various environmental changes throughout their service history (i.e., dry to wet, cold to hot). Environmental testing of such materials at less than 0° F. and greater than 100° F., and from 0-100% humidity, is desired to identify, quantify and monitor the properties of such materials before, during and/or after one or more uses to determine if any damage to the materials has occurred.

One type of sensor that has been used for environmental testing, acoustic emission (or AE) sensors, interprets the radiation of acoustic (or elastic) waves in solid materials into usable AE waveforms that help understand how the materials behave. Such acoustic (or elastic) waves occur when a material undergoes changes in its internal structure, for example as a result of crack formation or plastic deformation due to aging, temperature gradients or external mechanical forces. The waves generated by sources of acoustic emission are of practical interest in the fields of structural health monitoring, quality control, system feedback, process monitoring, analysis validation, and others, and may be used to detect, locate and characterize damage to the material. Acoustic emission sensors are therefore useful for detecting flaws and failures in materials and structures, and determining how to apply remedial solutions and repairs to resolve structural issues. In the aerospace field, acoustic emission sensing has been identified as a technology that can be scaled for enhanced fleet inspection from the laboratory setting, to the depot and to field applications. The focus is driven by the need to identify the existence of damage as a function of service hours for the fleet in order to make critical decisions regarding remaining life.

Acoustic emission sensors have been used to monitor aerospace and other structures. Traditional approaches for attaching acoustic emission sensors to the structure to be tested include using hot glue or magnetic clamping fixtures. Many commercially available holders for acoustic emission sensors are magnetic because acoustic emission has predominantly been done on metallic surfaces. Such magnetic holders will not function with non-metallic and non-magnetic composite materials. Hot glue does not have universal application, and does not work during environmental testing at temperatures less than −65° F. and greater than 160° F. due to poor surface adhesion. Another solution has been to permanently attach acoustic emission sensors to a test article, but this approach is not feasible when testing large numbers of test articles due to expense and extended dwell time (greater than 10 hours per sensor) for curing an adhesive to affix the sensors to the test article.

Non-metallic and non-magnetic materials, such as composite materials, are now used in the manufacture of a wide variety of structures due to their high strength and rigidity, low weight, corrosion resistance and other favorable properties. For example, composite materials have become widely used to manufacture aerospace structures and component parts for aerospace structures such as aircraft ribs, spars, panels, fuselages, wings, wing boxes, fuel tanks, tail assemblies and other component parts of an aircraft because they are lightweight and strong, and therefore provide fuel economy and other benefits. The traditional approaches for attaching acoustic emission sensors to such non-metallic and non-magnetic materials are not effective.

Accordingly, there is a need for improved means for holding or attaching acoustic emission sensors to non-metallic and non-magnetic materials, such as composites and ceramics, during environmental testing of such materials that provide advantages over known acoustic emission sensor holders.

SUMMARY

The foregoing purposes, as well as others, are achieved by an acoustic emission sensor holder that aligns and maintains the acoustic emission sensor flush with a surface of a non-metallic and non-magnetic material and is compatible with current ASTM standard test methods and test fixtures. The sensor holder provides the capability of keeping the sensor in contact with the material during extreme conditions, and therefore provides a pathway to obtain data across a wide range of environmental conditions that will be advantageous in progressive damage structural analysis, field inspection, material characterization and laboratory level experimental validation.

In accordance with one embodiment of the product of the disclosure, a holder for attaching an acoustic emission sensor to a non-metallic and non-magnetic material is disclosed. The holder is comprised of a tubular body having a closed top end and an open bottom end through which the sensor may be inserted into the tubular body. The closed top end is provided with a plurality of unitary flexible flaps angularly extending inwardly from an inner surface of the closed top end. An inner surface of the tubular body has a plurality of partial cylindrically-shaped spacers extending radially inward and upward from the open bottom end of the tubular body. The unitary flexible flaps and the spacers act together to fix the sensor within the tubular body and maintain its positioning within the holder.

In another embodiment of the product, a holder for attaching an acoustic emission sensor to a non-metallic and non-magnetic material comprises a cage that is removably secured to a retainer bracket that is affixed to the non-metallic and non-magnetic material. The cage has a tubular body with a closed top end and an open bottom end through which the sensor may be inserted. The tubular body of the cage has a plurality of capture tabs extending outwardly from an exterior surface of the tubular body proximate the interface surface. The retainer bracket is provided with a lower surface for attachment to the non-metallic and non-magnetic material, a top capture surface, and an engagement keyway disposed between the lower surface and the capture surface. The plurality of capture tabs on the cage is configured to be slidably engagable with the engagement keyway in the retainer bracket in a rotary motion providing a removable locking engagement. This permits a user to readily install and remove a sensor from the holder, and to maintain positioning of the holder when replacing a sensor.

In another embodiment, a system for affixing acoustic emission sensors to a non-metallic and non-magnetic material is disclosed. In the system, a plurality of the holders comprising a cage removably secured to a retainer bracket as described above are retained together at a frange periphery around each of the retainer brackets in each of the holders. The frange periphery permits ready separation of adjacent holders by any separation means such as snapping adjacent retainer brackets apart, or cutting them apart on the border between adjacent frange peripheries. At least one separator is provided in the system for connecting and positioning a plurality of the holders on the non-metallic and non-magnetic surface with predetermined spacing therebetween. Each separator has a plurality of arms positioned in a general X-formation. Ends of each of the arms in the separator are engageable with the retainer brackets, such that each arm has a retainer bracket of the holder attached thereto. The separator is made from a flexible material that permits positioning of a plurality of holders on flat surfaces or surfaces having a curved or other complex shape. In the system, a plurality of holders may be arranged in a desired configuration with predetermined spacing between the holders, and the desired configuration can then be moved from one non-metallic and non-magnetic material to another, or placed on a non-metallic and non-magnetic material to maintain positioning and permit ready replacement of sensors in the holders without disturbing the positioning of the holders.

In another aspect of the disclosure, a method for affixing acoustic emission sensors to a non-metallic and non-magnetic material is disclosed using the holder and system described above. In the method, a holder for an acoustic emission sensor is separated from a plurality of holders that are retained together at a frange periphery around each of the holders. The holder comprises a cage that is removably secured to a retainer bracket that is affixed to the non-metallic and non-magnetic material. The cage has a tubular body with a closed top end and an open bottom end through which the sensor may be inserted. The tubular body of the cage has a plurality of capture tabs extending outwardly from an exterior surface of the tubular body proximate the interface surface. The retainer bracket is provided with a lower surface for attachment to the non-metallic and non-magnetic material, a top capture surface, and an engagement keyway disposed between the lower surface and the capture surface. The plurality of capture tabs on the cage is configured to be slidably engagable with the engagement keyway in the retainer bracket in a rotary motion providing a removable locking engagement.

The lower surface of the retainer bracket of the separated holder is affixed to the non-metallic and non-magnetic material with, for example, vacuum bagging tape or other attachment means that can withstand environmental testing conditions. The cage may be removed from the retainer bracket prior to or after the retainer bracket is affixed to the non-metallic and non-magnetic material by rotating the cage out of the engagement keyway. An acoustic emission sensor may be inserted into the tubular body of the cage, and the cage is then installed on the retainer bracket by rotating the cage into the engagement keyway. A plurality of the holders may be positioned in various configurations on the non-metallic and non-magnetic surface with predetermined spacing therebetween by installing spacers having predetermined lengths and shapes between each of the holders, preferably before affixing the holders to the non-metallic and non-magnetic surface.

Other objects, features, and advantages of the various embodiments in the present disclosure will be explained in the following detailed description with reference to the appended drawings.

DETAILED DESCRIPTION

In the following detailed description, various embodiments of acoustic emission sensor holders that maintain the positioning and contact of acoustic emission sensors during environmental testing (less than 0° F., greater than 100° F., and between 0-100% humidity) of non-metallic and non-magnetic materials including, but not limited to, composite or ceramic materials, are described with reference to aerospace structures to illustrate the general principles in the present disclosure. It will be recognized by one skilled in the art that the present disclosure may be practiced in other analogous applications or environments and/or with other analogous or equivalent variations of the illustrative embodiments. For example, the disclosed acoustic emission sensor holders may be used for environmental testing of any type of non-metallic and non-magnetic materials in any industry and may be used with non-metallic and non-magnetic materials of varying shapes, sizes and surface contours including test materials for environmental testing in laboratory or other controlled settings, and completed structures that employ such non-metallic and non-magnetic materials, such as aerospace structures and vehicles, and any other structures for which environmental testing would be beneficial. Such environmental testing may be done during manufacture of the structures, after manufacture of the structures or during use of the structures. It should be noted that those methods, procedures, components, or functions which are commonly known to persons of ordinary skill in the field of the disclosure are not described in detail herein.

Figure 1:
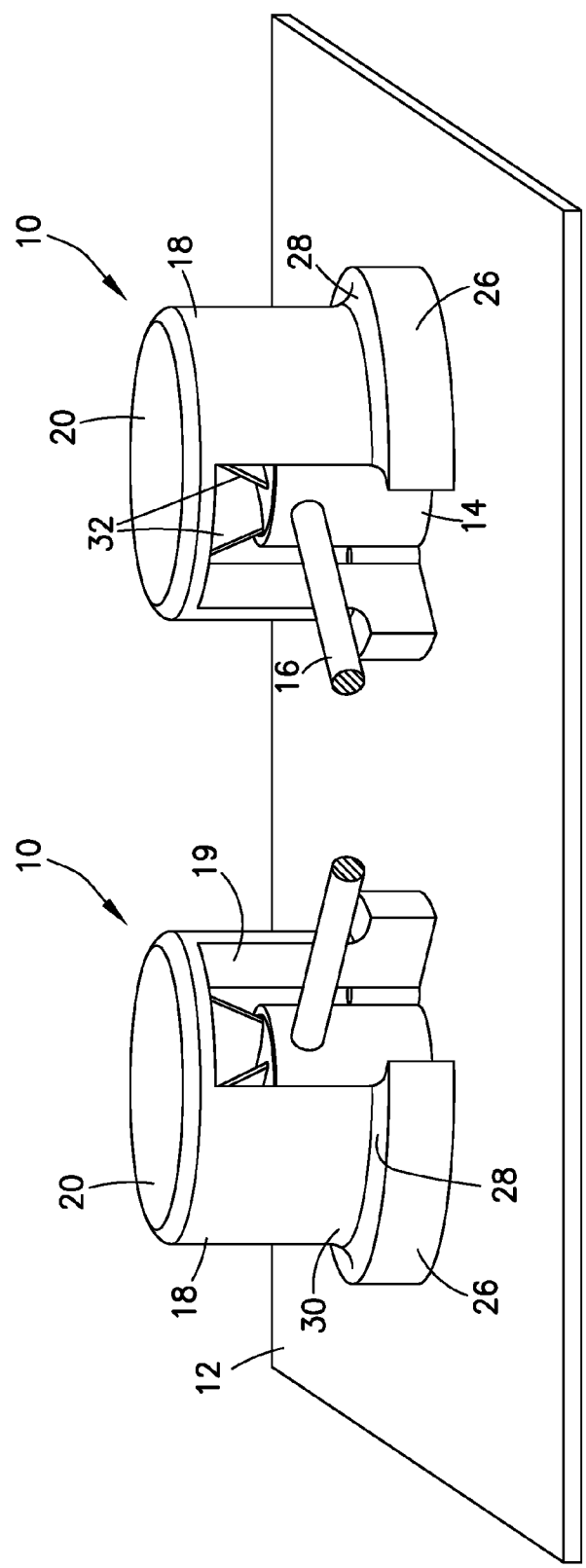
FIG. 1 is an illustration of a non-metallic and non-magnetic material having acoustic emission sensor holders and sensors affixed thereto prepared for environmental testing.
Figure 3:
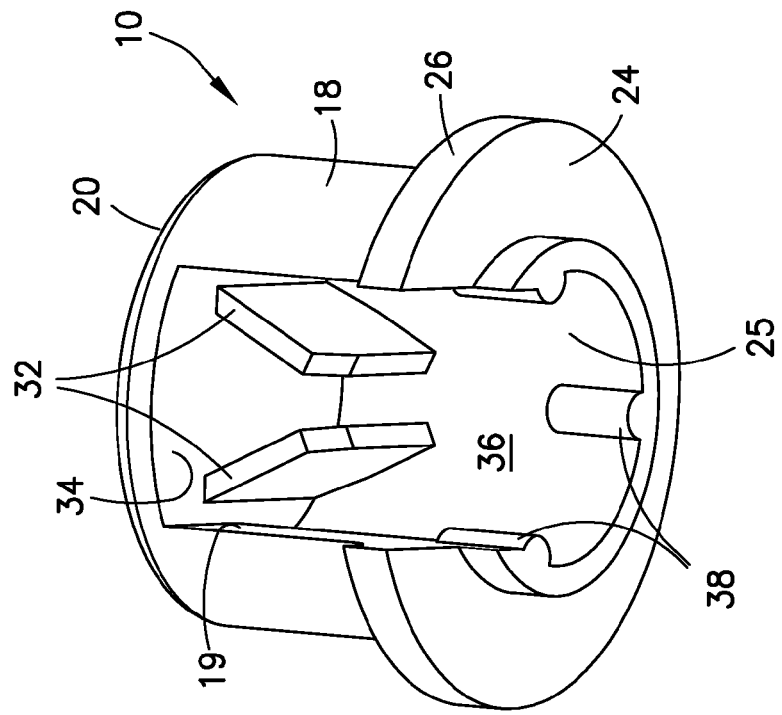
FIG. 3 is an illustration of another perspective view of the acoustic emission sensor holder shown in FIG. 2.
Figure 2:
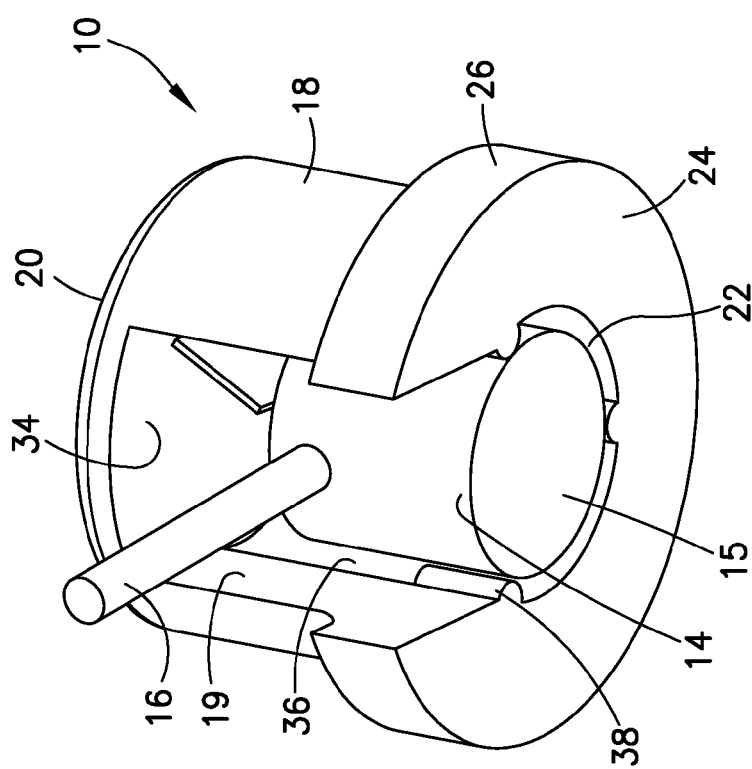
FIG. 2 is an illustration of a bottom, front and right side perspective view of an acoustic emission sensor holder with an acoustic emission sensor therein.

In FIGS. 1-3, an acoustic emission sensor holder 10 in accordance with one embodiment of the disclosure is shown affixed to a non-metallic and non-magnetic material 12 in the form of a test article or coupon (FIG. 1). The holder 10 has an acoustic emission sensor 14 installed therein with a sensor wire 16 (or electrical connection) protruding radially from the sensor 14 for connection to acoustic emission monitoring equipment (not shown). The holder 10 aligns a bottom surface 15 of the sensor 14 flush with a surface of the non-metallic and non-magnetic material 12 and permits use of current ASTM standard test methods and test equipment.

The holder 10 is in the shape of a tubular body 18 having a closed top end 20 and an open bottom end 22 that forms an interface surface 24 having an aperture 25 at the open bottom end 22 of the tubular body 18. The sensor 14 is insertable into the tubular body 18 through the aperture 25. A recess 19 in the tubular body 18 is peripherally open toward the aperture 25 at the open bottom end 22 for receiving the sensor wire 16 (or electrical connection) that protrudes radially from the sensor 14, and may form a rectangular shape as shown or any other shape. The tubular body 18 also has a base 26 forming a lip 28 on top of the base 26 and peripherally around an exterior surface 30 of the tubular body 18 that expands the size of the interface surface 24 at the open bottom end 22 to provide sufficient surface area for sealant tape (described below).

The closed top end 20 has a plurality of unitary flexible flaps 32 extending angularly inwardly from an inner surface 34 of the closed top end 20. Here, two of the unitary flexible flaps 32 are shown, each extending angularly inwardly toward each other to provide a force to push down on a top surface of the sensor 14 when the sensor 14 is installed into the holder 10. An interior surface 36 of the tubular body 18 has a plurality of spacers 38 extending radially inward proximate the open bottom end 22. The unitary flexible flaps 32 and the spacers 38 act together to fix the sensor 14 within the tubular body 18, and may be formed in any shape and size that provides the ability to fix the sensor 14 within the tubular body 18. For example, the spacers 38 may be formed in a partial cylindrical-shape protruding from the interior surface 36 of the tubular body 18 and extending upward from the open bottom end 22 as shown in the drawings, or the spacers 38 may be formed in a partial spherical-shape, oval-shape, or rectangular shape. In addition to the round cross-sectional shape of the tubular body 18 as shown, the holder 10 may also be formed to have a cross-sectional shape that is square, rectangular or another curved shape to accommodate different shaped sensors 14.

The holder 10 is preferably formed with a flexible material as a unitary three-dimensional (3-D) printed structure. 3-D printing, also known as stereolithography or additive manufacturing, is a printing technology that uses computer-controlled lasers to build three-dimensional structures from liquid polymers and other materials. The holders 10 disclosed herein are preferably made from a flexible material. Because the unitary flexible flaps 32 at the closed top end 20 of the tubular body 18 and the spacers 38 are made from a flexible material, the holder 10 can accommodate sensors 14 of varying heights and diameters.

The flexible material that forms the holder 10 and its parts should be ductile or flexible enough that the unitary flexible flaps 32 can bend but not snap when the sensor 14 is placed into the holder 10, and should have some stiffness to provide the downward force on the sensor 14. The flexible material should also be lightweight and have a wide range of operating temperatures to withstand environmental testing conditions, such as composite testing temperatures in the range from about −60° F. to 150° F. A flexible material having properties in the ranges shown in Table I could be used to form the holders described in the present disclosure:

TABLE I

MATERIAL PROPERTIES

| | |
|---|---|
| Flexural Modulus | 2.1 to 7.6 GPa (0.3 to 1.1 × $10^6$ psi) |
| Flexural Strength | 72 to 97 MPa (10 to 14 × $10^3$ psi) |
| Strength to Weight Ratio | 37 to 79 kN m/kg |

TABLE I-continued

MATERIAL PROPERTIES

| | |
|---|---|
| Tensile Strength: Ultimate (UTS) | 37 to 110 MPa (5.4 to 16 × $10^3$ psi) |
| Melting Temperature | Around 385° F. |
| Embrittlement | −168° C. |

Embrittlement is the temperature at which the material losses ductility, making it brittle. The melting temperature and embrittlement properties may be adjusted depending on the environmental conditions being tested. One material that has these properties and may be 3-D printed is ABS (Acrylonitrile-Butadiene-Styrene). ABS is a thermoplastic material further classified as styrenic plastic.

The holder 10 is affixed to the non-metallic and non-magnetic material 12 using vacuum bag, sealant tape, or a permanent sealant, which may be positioned on the interface surface 24 at the open bottom end 22 of the tubular body 18. Vacuum bag or sealant tapes should be able to withstand environmental testing conditions, and have short (less than 5 minutes) adhering time. Suitable tapes for this purpose are commercially available, for example, the sealant tapes available from the Airtech Advanced Materials Group of Airtech International, Inc., Huntington Beach, Calif., under the trade names GS-95, AT-199, AIRSEAL 2, AIRSEAL 3W, AIRSEAL DB, GS-100, AT-200Y, GS-213, GS-213 Tacky, GS-333, GS-213-3, GS-43MR, VBS-750 and A-800-3G. Such sealant tapes are typically available in rolls and are easy to cut and position in desired locations. When affixing the holder 10 to the non-metallic and non-magnetic material 12, it is also beneficial to apply vacuum grease or another coupling agent between the sensor 14 and the surface of the non-metallic and non-magnetic material 12 to couple the acoustic energy between the non-metallic and non-magnetic material 12 and the sensor 14 or more closely match the acoustic impedance of the disparate materials (e.g. to remove the air boundary by using a coupling agent).

Figure 5:
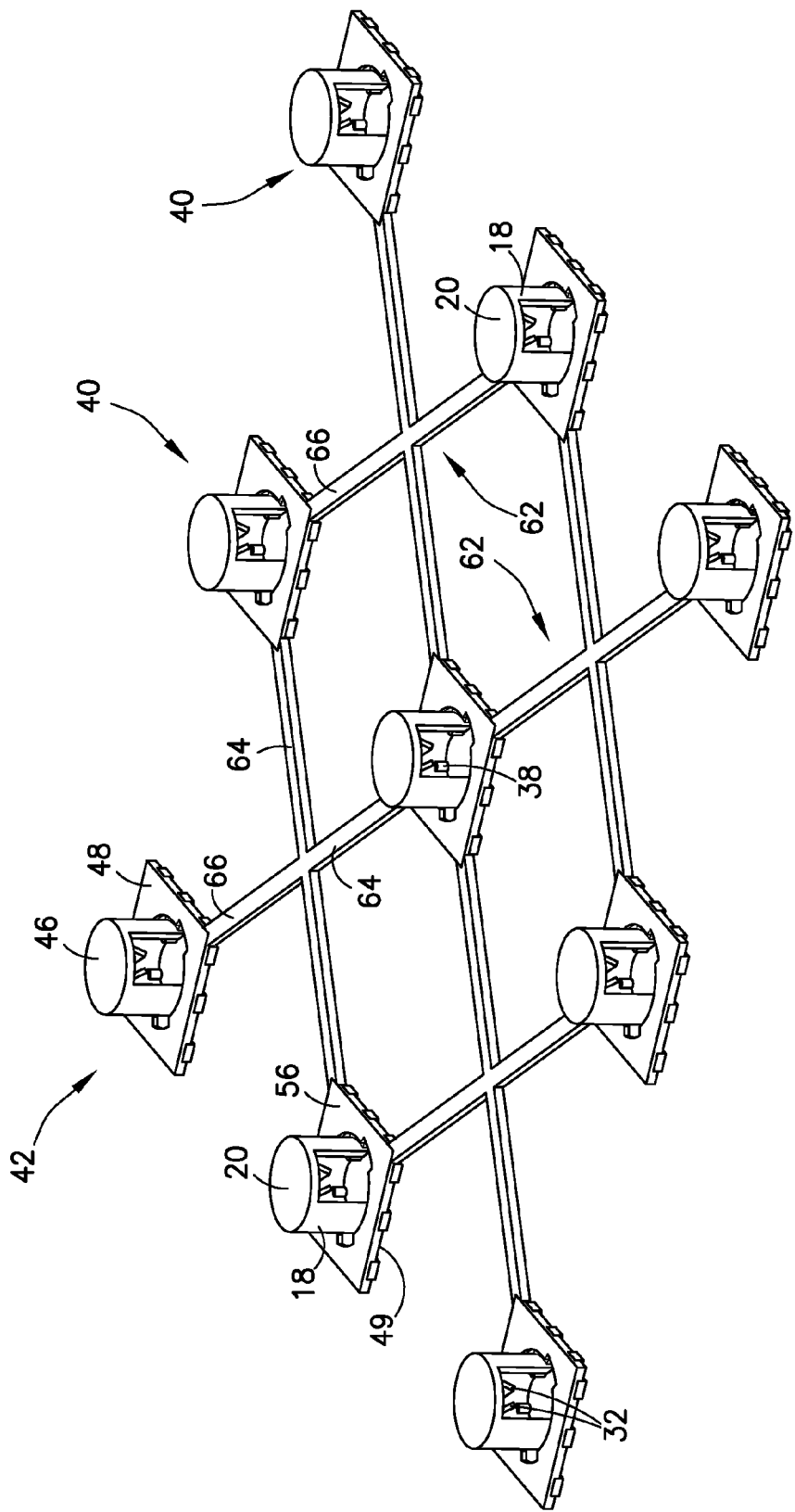
FIG. 5 is an illustration of an arrangement of a plurality of the acoustic emission sensor holder shown in FIG. 4 as part of a system of the disclosure.
Figure 6:
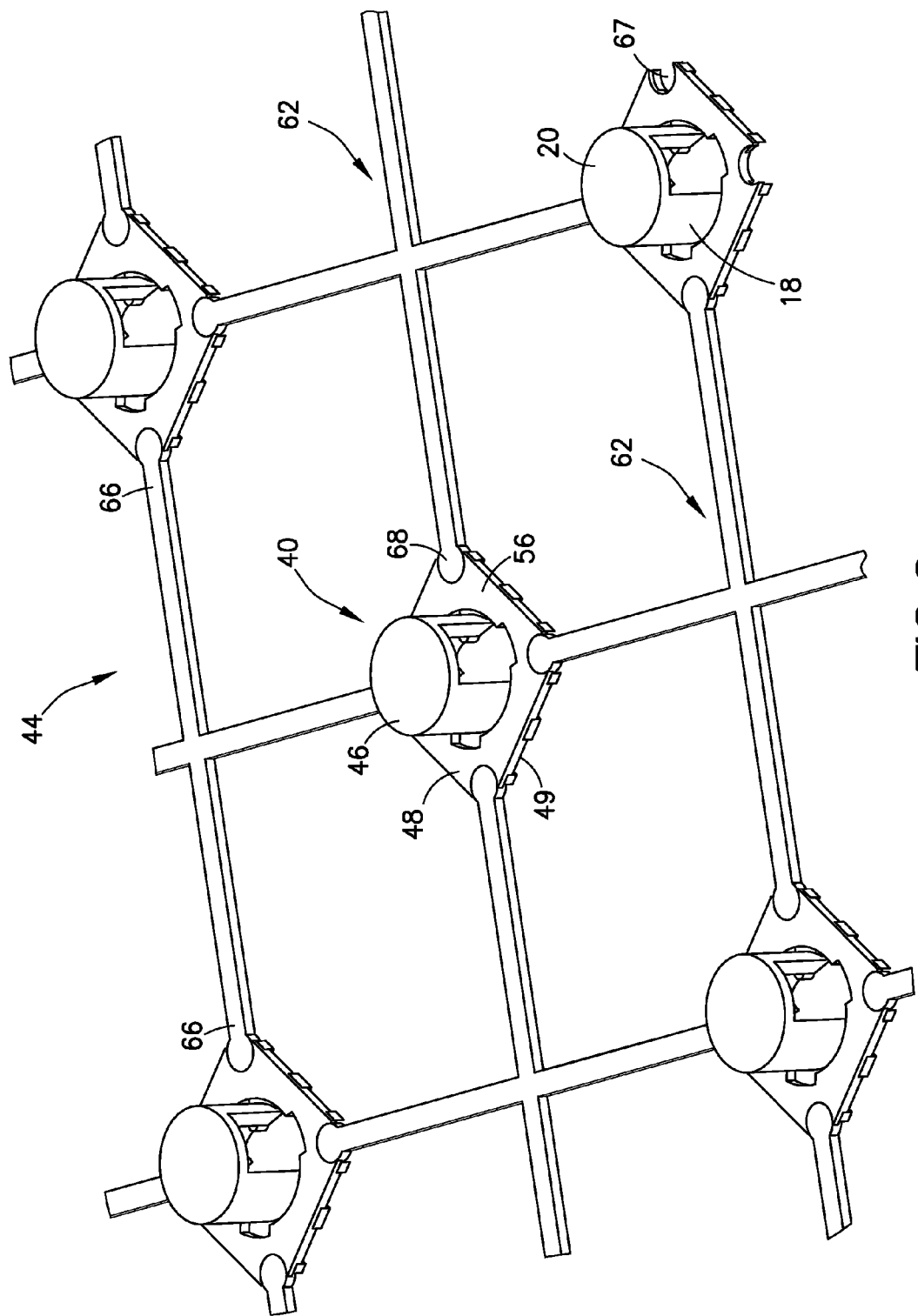
FIG. 6 is an illustration of another embodiment of an acoustic emission sensor holder.
Figure 7:
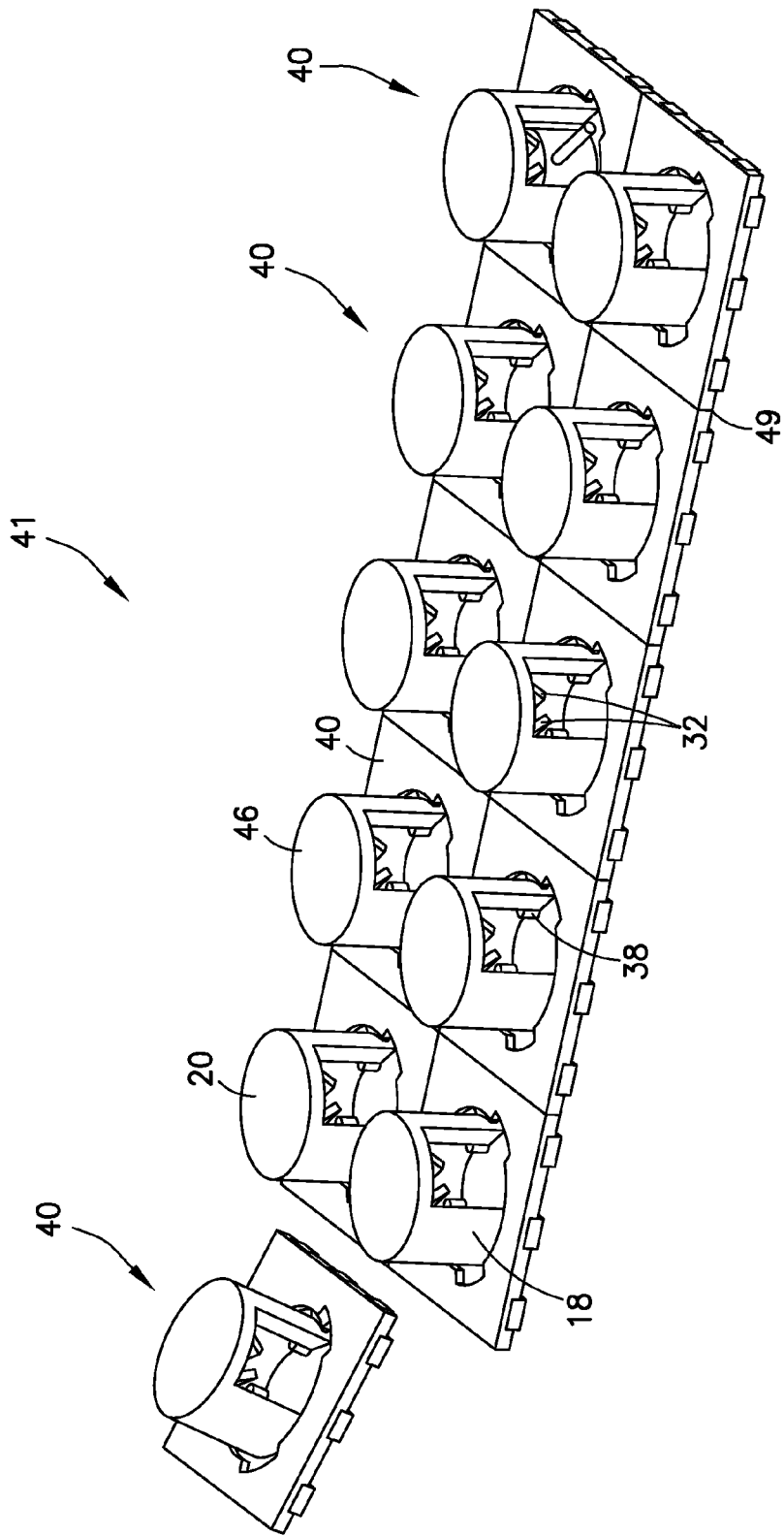
FIG. 7 is an illustration of a plurality of acoustic emission sensor holders as shown in FIG. 4 in a removable snap-fit configuration as part of a system of the disclosure.

An alternative holder 40 for attaching an acoustic emission sensor 14 to a non-metallic and non-magnetic material 12 and various systems 42, 44 using the alternative holder are shown in FIGS. 4-7. The alternative holder 40 comprises two parts—a cage 46 and a retainer bracket 48—removably engagable with each other by rotating the cage 46 into and out of engagement with retainer bracket 48. The cage 46 and the retainer bracket 48 are each unitary 3-D printed structures using the flexible materials described above, and may be manufactured individually or in groups of alternative holders 40, as shown in FIG. 7, to have a modular assemblage 41. In the modular assemblage 41, the plurality of alternative holders 40 are retained together at a frange periphery 49 around each of the retainer brackets 48 in each of the alternative holders 40. The frange periphery 49 permits separation of adjacent alternative holders 40. Each alternative holder 40 may be readily separated from the other alternative holders 40 in the modular assemblage 41 by snapping them apart or using a knife or scissor to cut them apart. The modular assemblage 41 of alternative holders 40 shown in FIG. 7 may also be used as a group on a non-metallic and non-magnetic material 12 to provide minimum spacing between sensors 14.

In this configuration, one or more the retainer brackets 48 may be affixed to a non-metallic and non-magnetic material 12 and a sensor 14 may be easily installed into or removed from the alternative holder 40 by simply rotating the cage 46 and removing it from the retainer bracket 48. This permits sensors 14 to be replaced while maintaining the positioning and configuration of the retainer brackets 48 (and thus the sensors 14) on the non-metallic and non-magnetic material 12. There is no need to remove the retainer bracket 48 from the non-metallic and non-magnetic material 12.

The cage 46 of the alternative holder 40 has a similar configuration to the holder 10 with a tubular body 18 having a closed top end 20 and an open bottom end 22 through which the sensor 14 is inserted into the tubular body 18. The closed top end 20 of the tubular body 18 has a plurality of unitary flexible flaps 32 angularly extending inwardly from an inner surface 34 of the closed top end 20, and an interior surface 36 of the tubular body 18 has a plurality of partial cylindrically-shaped spacers 38 extending radially inward and upward from the open bottom end 22 of the tubular body 18, for fixing the sensor 14 within the tubular body 18. As in the holder 10 shown in FIGS. 1-3, FIGS. 4-7 show a closed top end 20 with two of the unitary flexible flaps 32, each of the unitary flexible flaps 32 extending angularly inwardly toward each other to provide a downward force onto a top surface of the sensor 14 when the sensor is installed into the alternative holder 40.

Figure 4:
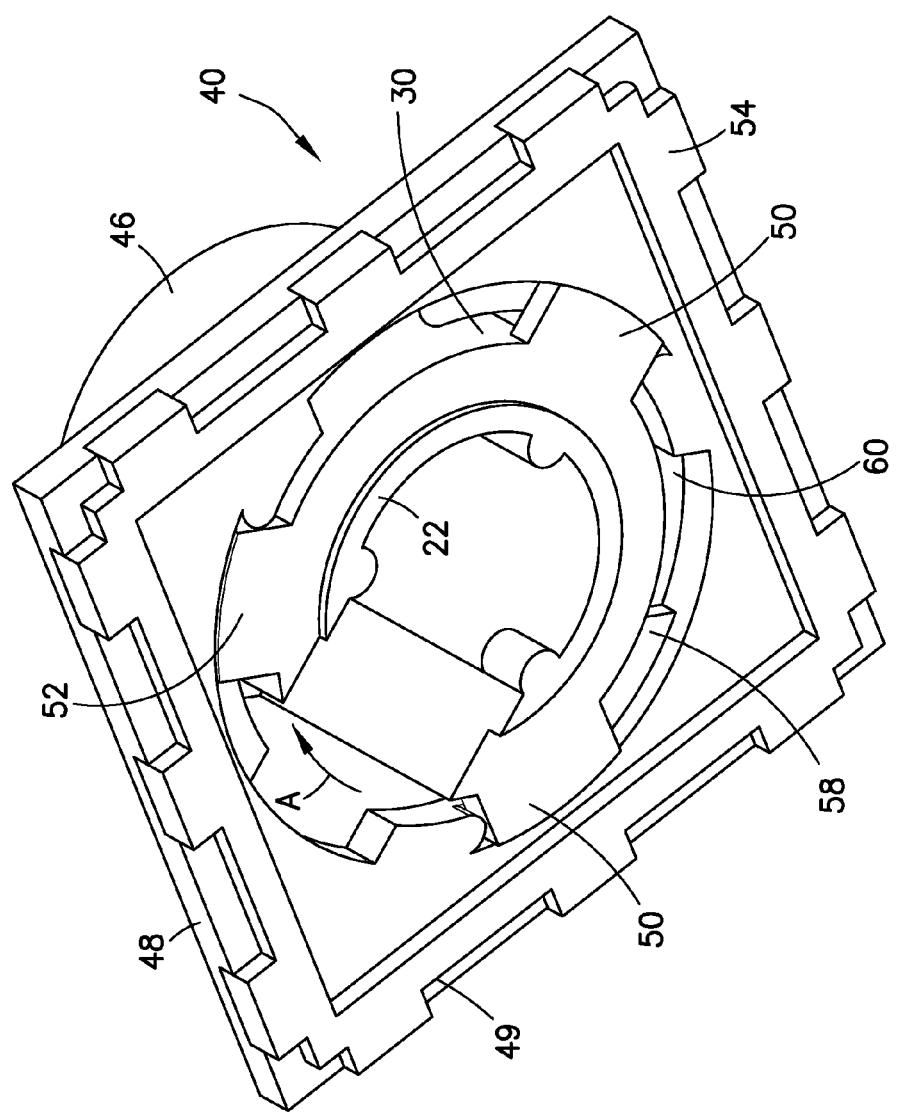
FIG. 4 is an illustration of another embodiment of an acoustic emission sensor holder.

The exterior surface 30 of the tubular body 18 near the open bottom end 22 of the cage 46 of the alternative holder 40 has a different configuration than that shown in the holder 10. Instead of the base 26, the cage 46 in the alternative holder 40 has a plurality of capture tabs 50 extending outwardly from the exterior surface 30 of the tubular body 18 to provide a generally flat surface 52 in a plane generally perpendicular to the plane of the tubular body 18 proximate the open bottom end 22. The capture tabs 50 are used to removably engage the cage 46 to the retainer bracket 48. FIG. 4 shows three capture tabs 50 positioned around the exterior surface 30 of the tubular body 18, but any number can be used depending on the diameter of the cage 46.

The retainer bracket 48 has a lower surface 54 for attachment to the non-metallic and non-magnetic material 12, a top capture surface 56 and an engagement keyway 58 disposed between the lower surface 54 and the capture surface 56 in an aperture 60 through the retainer bracket 48. The plurality of capture tabs 50 of the cage 46 are slidably engagable with the engagement keyway 58 in the retainer bracket 48 in a rotary motion (in the direction shown by arrow A in FIG. 4) to provide a removable locking engagement between the cage 46 and the retainer bracket 48. A stop may be provided in the engagement keyway 58 to provide notice to the user that the cage 46 is locked into the retainer bracket 48. In other embodiments, the cage 46 may be configured to snap into the retainer bracket 48 without rotating, and provide removal by squeezing the sides of the tubular body 18 or other means for removing a snap-fitted part.

The lower surface 54 of the retainer bracket has the form of an attach pad or leg. A sealant tape as described above is adhered to the lower surface 54 of the retainer bracket 48 for affixing the alternative holder 40 to a non-metallic and non-magnetic material 12.

Figure 9C:
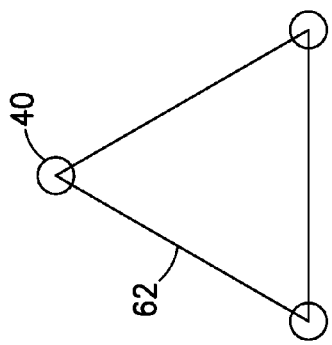
FIGS. 9A-9D are illustrations of alternative arrangements for a plurality of the acoustic emission sensor holders of this disclosure.
Figure 9D:
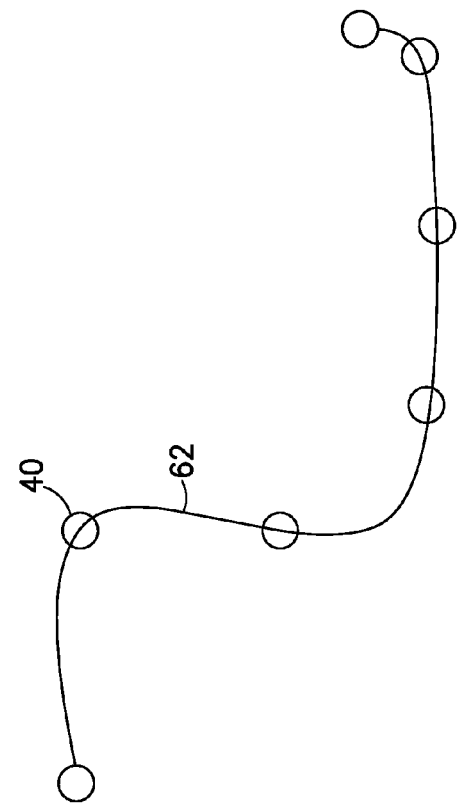
Figure 9A:
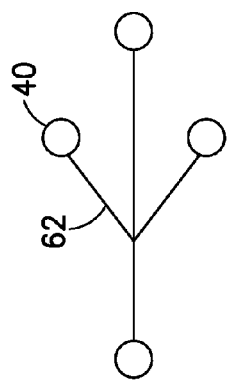
Figure 9B:
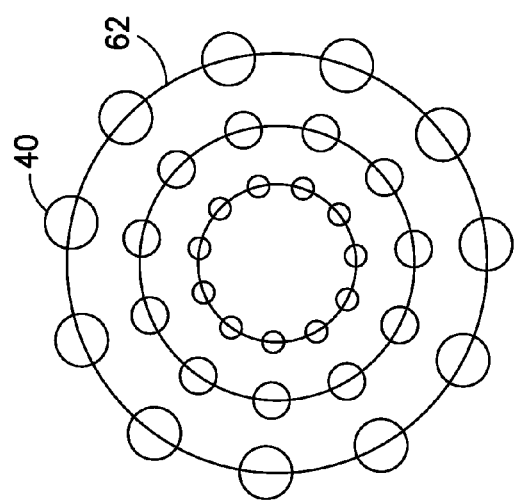

In the systems 42, 44 shown in FIGS. 5-6 the alternative holders 40 are separated from the modular assemblage 41 shown in FIG. 7 and arranged in an array with predetermined spacing. The predetermined spacing between each of the alternative holders 40 is provided by a separator 62 having a plurality of arms 64 positioned, for example, in an X-formation generally perpendicular to each other. Configurations other than X-formations may also be used, such as a straight separator without a crossing arm, or a separator configured to have a spider shape, a triangle, a circular pattern or a free-form pattern. Examples of such alternative patterns are shown in FIGS. 9A-9D. The shape, size and configuration options should be adaptive to the structural requirements. For example, when a repair patch is used for aerospace structures comprising a non-metallic and non-magnetic material 12, the repair patch is typically in the form of an ellipsoidal or circular geometry. The separators 62 could be configured to provide a network extending around the perimeter to bound the patch. There are multiple array geometries that may be conceived wherein the density of sensors in a particular area may be adjusted based on structural need, which may be due to known damage morphology or size, structure features and geometry, or the need for quick modifications of the sensor network during use. The systems 42, 44 and variations thereof that are disclosed herein are readily adaptive to meet such structural needs. In another example, a long strip or rope of sensors, as shown in FIG. 9D, may be provided to wrap along a wing, spar, rib, skin of an aircraft or any other type of surface, and be positioned in any desired configuration.

Ends 66 of each of the arms 64 are engageable with a plurality of retainer brackets 48 for positioning a plurality of the alternative holders 40 on the non-metallic and non-magnetic material 12 with predetermined spacing therebetween. A plurality of separators 62 is used with a plurality of alternative holders 40 to make a wide variety of configurations for the array of alternative holders 40. The separators 62 comprise a flexible material (as described above) that permits positioning of the plurality of alternative holders 40 with predetermined spacing on flat surfaces, curved surfaces or surfaces of a non-metallic and non-magnetic material 12 with complex geometric shapes, and permits the entire configuration of sensors to actuate and move with the surface (for example, during fatigue loading, or during actual service use, or such that the entire configuration of sensors may be used between two parts that actuate with respect to each other) The separators 62 may be attached to the alternative holders 40 in any way known for attaching flexible materials together. For example, adhesives may be used, the ends 66 of the arms 64 can be configured to snap together or to mate together in other ways. The system of FIG. 5 shows an embodiment that uses an adhesive to affix the ends 66 of the arms 64 to corners of the frange periphery 49 of the retainer brackets 48. The system of FIG. 6 shows an embodiment that uses a snap-fit attachment means where the corners of the retainer bracket 48 have a bulbous cutout 67 that accommodates a bulbous end 68 of the arms 64 of the separator 62.

Figure 8:
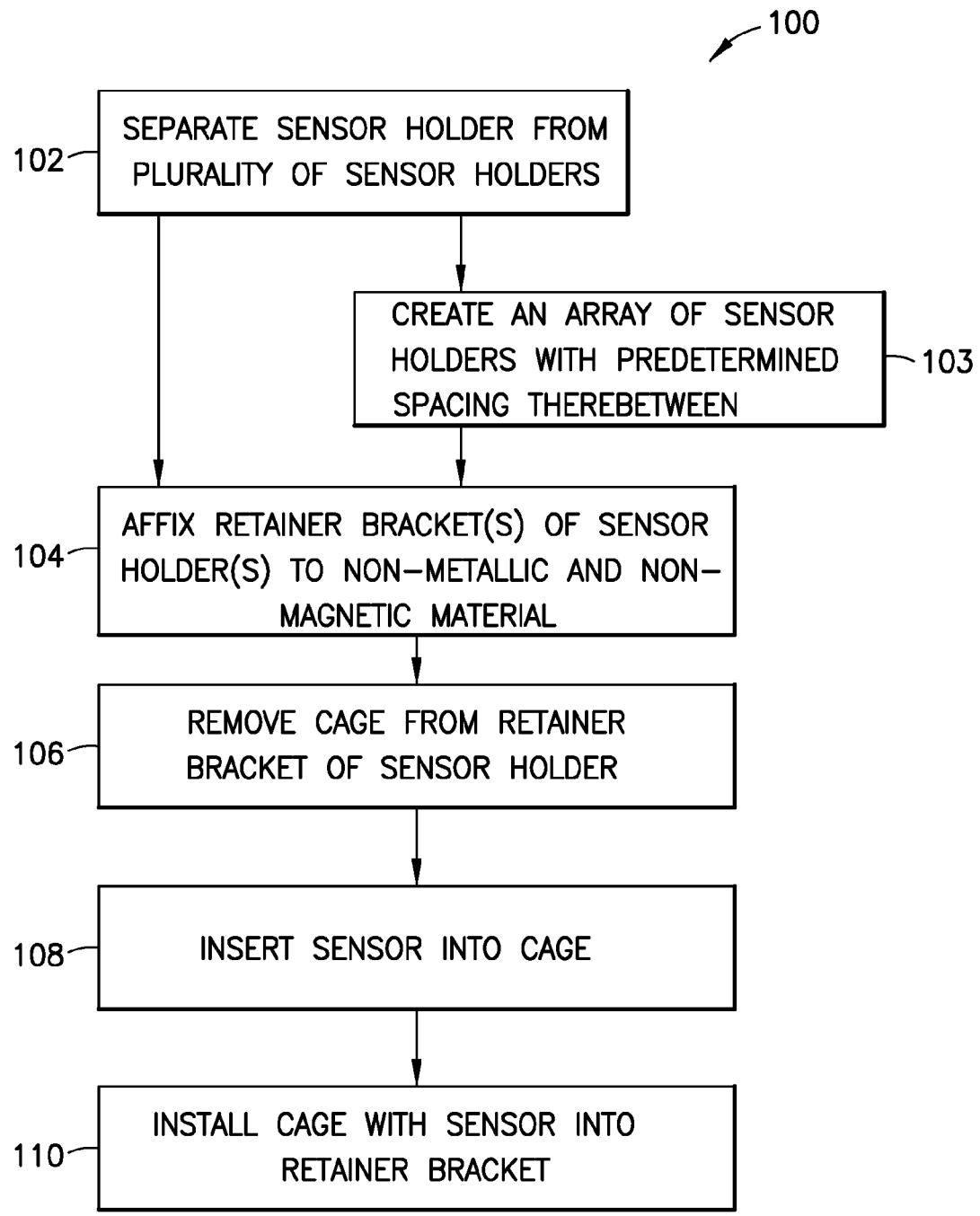
FIG. 8 is a block diagram of a method of the disclosure.

In a method 100 for affixing acoustic emission sensors to a non-metallic and non-magnetic material, referring to FIG. 8, a plurality of alternative holders 40 are used with a plurality of separators 62 to form a sensor holder array that is affixed to a non-metallic and non-magnetic material 12, which may be a test article or a completed structure, before, during or after manufacture and use of such structure. In step 102 of the method, an alternative holder 40 is separated from a plurality of alternative holders 40 that are retained together in a modular assemblage 41 at a frange periphery 49 around the retainer brackets 48 of each of the alternative holders 40. In step 104, the retainer bracket 48 of the separated alternative holder is affixed to the non-metallic and non-magnetic material with a sealant tape as described above. In step 106, the cage 46 of the alternative holder 40 is removed from the retainer bracket 48 by rotating the cage 46 out of the engagement keyway 58. A sensor 14, such as an acoustic emission sensor, is then inserted into the tubular body 18 of the cage 46 in step 108 and, in step 110, the cage 46 with the installed sensor 14 is engaged with the retainer bracket 48 by rotating the cage into the engagement keyway 58 in the direction shown by the arrow A in FIG. 4.

In a further embodiment of the method 100, the step 103 may be added to create an array of sensor holders with predetermined spacing between each sensor holder. In step 103A, the retainer bracket 48 of one of the alternative holders 40 is engaged with one end 66 of a separator 62 having a plurality of arms 64 positioned in an X-formation, and the retainer bracket 48 of another of the alternative holders 40 is engaged at another end 66 of the separator 62. The array of alternative holders 40 with predetermined spacing is then affixed to the non-metallic and non-magnetic material 12 in step 104.

A kit may be provided that includes a plurality of alternative holders 40 connected together in a modular assemblage 41, at least one separator 62 and sealant tape.

The holders and separators disclosed herein provide a cost and time efficient system and method for affixing sensors, such as acoustic emission sensors, to a non-metallic and non-magnetic material. The holders do not require additional assembly such as springs and screws, and the systems are scalable to account for variations in sensor size and test configurations, and may be used in a wide range of temperature conditions suitable for environmental testing at testing scales ranging from test article or coupon level to complete structures, such as aircraft, and any testing condition, from laboratory to field/depot, thus providing acoustic emission data from diverse environmental conditions.

Many other modifications and variations may of course be devised given the above description of various embodiments for implementing the principles in the present disclosure. For example, and without limitation, the geometry of the sensor holder 10 and the cage 46 and retainer bracket 48 of the alternative sensor holder 40 may be designed to conform to the size and geometry of any type of acoustic sensor 14. The retainer bracket 48 may be fabricated and unitized in any modular assembly to provide different group assemblages, the separator lengths may be altered to form any array shape or geometry to cover targeted structural areas with higher or lower density of sensor placement. The adherent (such as vacuum tape etc.) may be pre-applied to the retainer bracket 48 on an individual or on a group basis and sealed so as to preserve the tacky/sticky end for adhering to a surface of a non-metallic and non-magnetic material 12.—This embodiment would be provided as a pre-packaged kit containing all required parts for rapid use. The arms 64 of the separators 62 may be designed so as to snap, clip, press, into place into the retainer bracket 48. In other embodiments, the retainer bracket 48 and cage 46 could be a monolithic/1-piece construction to reduce the number of parts for a specific acoustic sensor type/geometry. The width and geometry of the separator 62 may be further designed to provide non-symmetric configurations of any network or array geometry (such as spider-web, circular, triangular, diamond, linear, or curved as shown in FIGS. 9A-9D, or any other configuration). Such non-symmetric configurations may be designed to cover a desired structural geometry/configuration (e.g. to cover the surface area of a doubler, the perimeter of a known damage region, or boundaries of a repair patch), with a mix of cages 46 and retainer brackets 48 available to create a network of multiple sensor sizes. The separator 62 and retainer bracket 48 may also be formed as a monolithic/1-piece unit. It is intended that all such modifications and variations be considered as within the spirit and scope of this disclosure, as defined in the following claims.

The invention claimed is:

1. A holder for attaching an acoustic emission sensor to a non-metallic and non-magnetic material, the holder comprising a tubular body having a closed top end and an open bottom end through which the sensor is insertable into the tubular body, the closed top end having a plurality of unitary flexible flaps angularly extending inwardly from an inner surface of the enclosed top end, an inner surface of the tubular body having a plurality of spacers extending radially inward proximate the bottom end of the tubular body, the unitary flexible flaps and the spacers fixing the sensor within the tubular body.

2. The holder of claim 1, wherein the closed top end has two of the unitary flexible flaps, each of the unitary flexible flaps extending angularly inwardly toward each other to provide a downward force onto a top surface of the sensor when the sensor is installed into the holder.

3. The holder of claim 1, wherein the holder is a unitary 3-D printed structure.

4. The holder of claim 1, further comprising a recess in the tubular body that is peripherally open toward the open bottom end for receiving an electrical connection that protrudes radially from the sensor.

5. The holder of claim 1, further comprising a base forming a lip peripherally around an exterior surface of the tubular body proximate the open bottom end to provide an interface surface for engaging the non-metallic and non-magnetic surface.

6. A holder for attaching an acoustic emission sensor to a non-metallic and non-magnetic material, the holder comprising:
    a cage having a tubular body with a closed top end and an open bottom end through which the sensor is insertable into the tubular body, the closed top end of the tubular body having a plurality of unitary flexible flaps angularly extending inwardly from an inner surface of the closed top end, and an inner surface of the tubular body having a plurality of spacers extending radially inward proximate the open bottom end of the tubular body, the unitary flexible flaps and the spacers fixing the sensor within the tubular body, the tubular body of the cage having a plurality of capture tabs extending outwardly from an exterior surface of the tubular body proximate the open bottom end; and
    a retainer bracket having a lower surface for attachment to the non-metallic and non-magnetic material, a top capture surface and an engagement keyway disposed between the lower surface and the capture surface;
    the plurality of capture tabs of the cage slidably engagable with the engagement keyway in the retainer bracket in a rotary motion providing a removable locking engagement.

7. The holder of claim 6, further comprising an attach pad positioned on the lower surface of the retainer bracket for affixing the holder to the non-metallic and non-magnetic material.

8. The holder of claim 6, wherein the closed top end has two of the unitary flexible flaps, each of the unitary flexible flaps extending angularly inwardly toward each other to provide a downward force onto a top surface of the sensor when the sensor is installed into the holder.

9. The holder of claim 6, wherein the cage and the retainer bracket are each unitary 3-D printed structures.

10. A system for affixing acoustic emission sensors to a non-metallic and non-magnetic material comprising a plurality of the holders of claim 6 retained together at a frange periphery around each of the retainer brackets in each of the holders, the frange periphery permitting separation of adjacent holders.

11. The system of claim 10, further comprising a separator engageable with the retainer bracket for positioning a plurality of the holders on the non-metallic and non-magnetic surface with predetermined spacing therebetween.

12. The system of claim 11, wherein the separator comprises a flexible material that permits positioning of the plurality of holders with predetermined spacing on a flat or curved surface of the non-metallic and non-magnetic material.

13. The system of claim 10, further comprising an attach pad positioned on the lower surface of the retainer bracket for affixing the holder to the non-metallic and non-magnetic material.

14. The system of claim 10, wherein the cage and the retainer bracket are each unitary 3-D printed structures.

15. A method for affixing an acoustic emission sensor to a non-metallic and non-magnetic material comprising the steps of:
  separating a holder for the acoustic emission sensor from a plurality of holders retained together at a frange periphery around each of the holders, the holder comprising: a cage having a tubular body with a closed top end and an open bottom end through which the sensor is insertable into the tubular body, the closed top end of the tubular body having a plurality of unitary flexible flaps angularly extending inwardly from an inner surface of the closed top end, and an inner surface of the tubular body having a plurality of spacers extending radially inward proximate the open bottom end of the tubular body, the unitary flexible flaps and the spacers fixing the sensor within the tubular body, the tubular body of the cage having a plurality of capture tabs extending outwardly from an exterior surface of the tubular body proximate the open bottom end; and a retainer bracket having a lower surface for attachment to the non-metallic and non-magnetic material, a top capture surface and an engagement keyway disposed between the lower surface and the capture surface; the plurality of capture tabs of the cage slidably engagable with the engagement keyway in the retainer bracket in a rotary motion providing a removable locking engagement;
  affixing the retainer bracket of the holder to the non-metallic and non-magnetic material;
  removing the cage from the retainer bracket by rotating the cage out of the engagement keyway;
  inserting the acoustic emission sensor into the tubular body of the cage; and
  installing the cage on the retainer bracket by rotating the cage into the engagement keyway.

16. The method of claim 15, further comprising the steps of 3-D printing the cage and the retainer bracket.

17. The method of claim 15, further comprising the step of engaging the retainer bracket of one of the holders with one end of a separator, and engaging the retainer bracket of another of the holders at another end of the separator for positioning the plurality of the holders on the non-metallic and non-magnetic surface with predetermined spacing therebetween.

* * * * *